United States Patent
Jiang et al.

(10) Patent No.: US 11,987,587 B2
(45) Date of Patent: May 21, 2024

(54) CHIRAL BISAMINO-ETHER COMPOUNDS, AND METHOD OF PREPARATION AND USE THEREOF

(71) Applicants: JINAN UNIVERSITY, Guangzhou (CN); THE CHINESE UNIVERSITY OF HONG KONG, Hong Kong (CN)

(72) Inventors: Xiaojian Jiang, Guangzhou (CN); Ying Yeung Yeung, Hong Kong (CN)

( * ) Notice: Subject to any disclaimer, the term of this patent is extended or adjusted under 35 U.S.C. 154(b) by 0 days.

(21) Appl. No.: 16/602,382

(22) PCT Filed: Mar. 5, 2019

(86) PCT No.: PCT/CN2019/000044
§ 371 (c)(1),
(2) Date: Sep. 27, 2019

(87) PCT Pub. No.: WO2020/007017
PCT Pub. Date: Jan. 9, 2020

(65) Prior Publication Data
US 2022/0162219 A1  May 26, 2022

(51) Int. Cl.
| | |
|---|---|
| *C07D 401/12* | (2006.01) |
| *C07D 401/14* | (2006.01) |
| *C07D 403/14* | (2006.01) |
| *C07D 487/04* | (2006.01) |
| *C07D 491/048* | (2006.01) |

(52) U.S. Cl.
CPC ....... *C07D 491/048* (2013.01); *C07D 401/12* (2013.01); *C07D 401/14* (2013.01); *C07D 403/14* (2013.01); *C07D 487/04* (2013.01)

(58) Field of Classification Search
CPC ... C07D 401/14; C07D 401/12; C07D 403/14
See application file for complete search history.

*Primary Examiner* — Brian E McDowell
(74) *Attorney, Agent, or Firm* — Panterrain IP Law; Charles Liu

(57) ABSTRACT

The present invention provides novel chiral bisamino-ether compounds, and method of preparation and use thereof. The chiral bisamino-ether compounds have the structure of formula (I). The method of preparation includes: using chiral aminomethanol compounds as starting materials to react with halogenated aryl compounds in the presence of a base to give a variety of chiral bisamino-ether compounds. The novel chiral bisamino-ether compounds can be used for asymmetric fluorocyclization of unsaturated heterocyclic compounds with excellent enantioselectivity and great potentials for industrial applications.

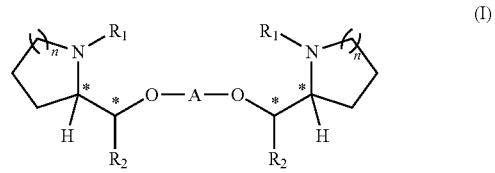

(I)

4 Claims, No Drawings

CHIRAL BISAMINO-ETHER COMPOUNDS, AND METHOD OF PREPARATION AND USE THEREOF

FIELD OF THE INVENTION

The present invention relates to novel chiral bisamino-ether compounds, and method of preparation and use thereof. Specifically, chiral aminomethanol compounds are used as starting materials to react with halogenated aryl compounds in the presence of a base to give a variety of chiral bisamino-ether compounds. The novel chiral bisamino-ether compounds can be used for asymmetric fluorocyclization of unsaturated heterocyclic compounds with excellent enantioselectivity and great potentials for industrial applications.

BACKGROUND OF THE INVENTION

In the past few decades, natural bis-quinine or bis-quinidine has been used as a catalyst or reactant in a variety of asymmetric reactions to prepare important chiral compounds (Behrens, C. H.; Sharpless, K. B. Aldrichimica Acta 1983, 16, 67; Kolb, H. C.; van Nieuwenhze, M. S.; Sharpless, K. B. Chem. Rev. 1994, 94, 2483; Li, G G.; Chang, H. T.; Sharpless, K. B. Angew. Chem. Int. Ed. Engl. 1996, 35, 451; Jaganathan, A.; Garzan, A.; Whitehead, D. C.; Staples, R. J.; Borhan, B. Angew. Chem. Int. Ed. Engl. 2011, 50, 2593; Whitehead, D. C.; Yousefi, R.; Jaganathan, A.; Borhan, B. J. Am. Chem. Soc. 2010, 132, 3298; Lozano, O.; Blessley, G.; del Campo, T. M.; Thompson, A. L.; Giuffredi, G. T.; Bettati, M.; Walker, M.; Borman, R.; Gouverneur, V. Angew. Chem. Int. Ed. Engl. 2011, 50, 8105; Yu, P. A. Handbook of Reagents for Organic Synthesis: Catalytic Oxidation Reagents 2013, 483).

In the past, the materials of such bis-quinine or bis-quinidine compounds were derived from the natural product of quinine or quinidine. However, the quinine or quinidine, as a natural product, has a single structure rather than being a pair of mirror-image of enantiomers. Consequently, the compounds are difficult to be structurally modified, and thus that the R and S enantiomeric products cannot be ensured to have the same ee value.

SUMMARY OF THE INVENTION

To overcome the above disadvantages of the natural products of quinine or quinidine, the present invention provided synthesis of various of chiral aminomethanol intermediates 1 using D or L type amino acids as starting materials (Jiang, X.; Tan, C K; Zhou, L.; Yeung, Y.-Y. Angew. Chem. Int. Ed. Engl. 2012, 51, 7771). For example, the natural L-proline or D-proline, which is inexpensive and readily available, was used as a starting material to carry out oxidation and Grignard reaction to give the compound C or F each having two chiral centers, and then through column chromatography purification, four chiral aminomethanol compounds 1 having different stereo configurations can be obtained (as shown in the scheme below) as the raw materials in the present invention. The variability of the groups $R_1$ and $R_2$ allows the final product chiral bisamino-ether compound (I) of the present invention to have multiple tunable sites to form a variable spatial structure for the needs of different reactions, and the presence of D and L types of amino acids shall ensure that both R and S enantiomeric products with the same ee value can be obtained. It is indicated that the chiral bisamino-ether compounds (I) of the present invention have broad industrial utilities.

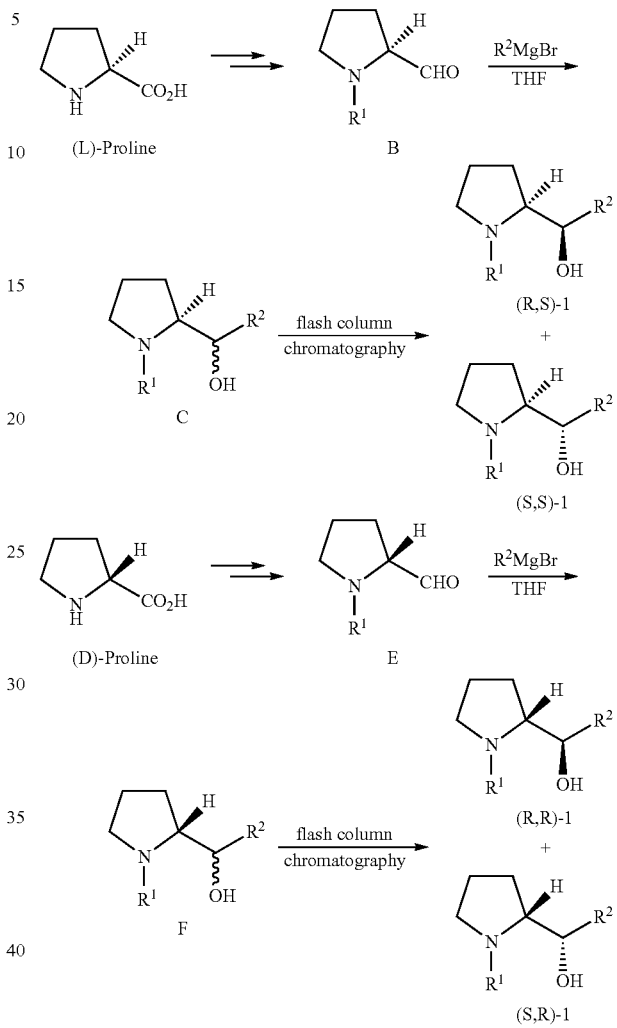

Therefore, in order to solve the problems associated with the natural bis-quinine or bis-quinidine compounds, the present invention provides novel chiral bisamino-ether compounds, and method of preparation and use thereof. The novel chiral bisamino-ether compounds can be used for asymmetric fluorocyclization of unsaturated heterocyclic compounds with excellent enantioselectivity for broad industrial applications.

In one aspect, the present invention provides a chiral bisamino-ether compound having the structure of formula (I):

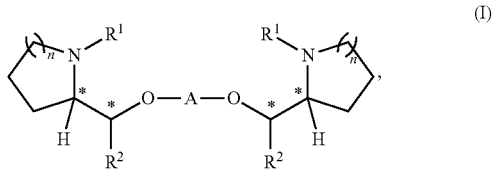

wherein:
n=1 or 2; chiral center * has (R) or (S) configuration; and

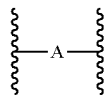

is one of the following moieties:

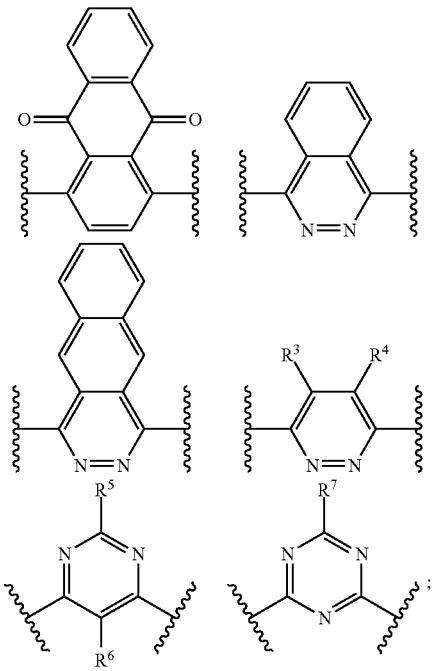

$R^1$ is selected from the group consisting of hydrogen, $C_1$-$C_8$ alkyl, $C_1$-$C_9$ unsaturated alkyl, haloalkyl, $C_1$-$C_8$ alkoxyl, phenyl, $C_1$-$C_8$ alkyl substituted phenyl, halophenyl, hydroxyl substituted phenyl, amino substituted phenyl, di($C_1$-$C_8$ alkyl)amino substituted phenyl, $C_1$-$C_8$ alkoxyl substituted phenyl, $C_1$-$C_8$ acyl substituted phenyl, ($C_1$-$C_8$ acyl)amino substituted phenyl, $C_2$-$C_8$ ester group-substituted phenyl, and $C_2$-$C_8$ acyloxyl substituted phenyl;

$R^2$ is selected from the group consisting of hydrogen, $C_1$-$C_8$ alkyl, $C_1$-$C_9$ unsaturated alkyl, haloalkyl, $C_1$-$C_8$ alkoxyl, phenyl, $C_1$-$C_8$ alkyl substituted phenyl, halophenyl, hydroxyl substituted phenyl, amino substituted phenyl, di($C_1$-$C_8$ alkyl)amino substituted phenyl, $C_1$-$C_8$ alkoxyl substituted phenyl, $C_1$-$C_8$ acyl substituted phenyl, ($C_1$-$C_8$ acyl)amino substituted phenyl, $C_2$-$C_8$ ester group-substituted phenyl, $C_2$-$C_8$ acyloxyl substituted phenyl, naphthyl, pyridyl, quinolyl, isoquinolinyl, furyl, and thienyl;

$R^3$, $R^4$, $R^5$, $R^6$ and $R^7$ may be the same or different, and are each independently selected from the group consisting of hydrogen, $C_1$-$C_8$ alkyl, $C_1$-$C_9$ unsaturated alkyl, haloalkyl, $C_1$-$C_8$ alkoxyl, $C_1$-$C_8$ acyl, $C_2$-$C_8$ acyloxyl, $C_2$-$C_8$ ester group, ($C_1$-$C_8$ acyl)amino, di($C_1$-$C_8$ alkyl)amino, halogen, amino, phenyl, $C_1$-$C_8$ alkyl substituted phenyl, halophenyl, hydroxyl substituted phenyl, amino substituted phenyl, di($C_1$-$C_8$ alkyl) amino substituted phenyl, $C_1$-$C_8$ alkoxyl substituted phenyl, $C_1$-$C_8$ acyl substituted phenyl, ($C_1$-$C_8$ acyl) amino substituted phenyl, $C_2$-$C_8$ ester group-substituted phenyl, $C_2$-$C_8$ acyloxyl substituted phenyl, naphthyl, pyridyl, quinolyl, isoquinolinyl, furyl and thienyl.

In the chiral bisamino-ether compound (I):
the $C_1$-$C_8$ alkyl is methyl, ethyl, n-propyl, isopropyl, cyclopropyl, n-butyl, isobutyl, sec-butyl, tert-butyl, cyclobutyl, n-pentyl, isoamyl, neopentyl, sec-pentyl, tert-amyl, cyclopentyl, n-hexyl, isohexyl, neohexyl, sec-hexyl, tert-hexyl, cyclohexyl, n-heptyl, isoheptyl, neoheptyl, n-heptyl, tert-heptyl, cycloheptyl, n-octyl, isooctyl, neooctyl, sec-octyl, tert-octyl, or cyclooctyl;

the $C_1$-$C_9$ unsaturated alkyl is allyl, 2-methylpropyl, cis-n-butenyl, trans-2-butenyl, 3,3-dimethylallyl, cis-2-pentenyl, trans-2-pentenyl, propargyl, benzyl, or 1-phenyl-1-propenyl;

the haloalkyl is halogenated alkyl with halogen being fluorine, chlorine, bromine or iodine;

the $C_1$-$C_8$ alkoxy is methoxyl, ethoxyl, n-propoxyl, isopropoxyl, cyclopropoxyl, n-butoxyl, iso-butoxyl, sec-butoxyl, tert-butoxyl, cyclobutoxyl, n-pentyloxyl, iso-pentyloxyl, neo-pentyloxyl, sec-pentyloxyl, tert-pentyloxyl, cyclopentyloxyl, n-hexyloxyl, iso-hexyloxyl, neo-hexyloxyl, sec-hexyloxyl, tert-hexyloxyl, cyclohexyloxyl, n-heptyloxyl, iso-heptyloxyl, neo-heptyloxyl, sec-heptyloxyl, tert-heptyloxyl, cycloheptyloxyl, n-octyloxyl, iso-octyloxyl, neo-octyloxyl, sec-octyloxyl, tert-octyloxyl, or cyclooctyloxyl;

the $C_1$-$C_8$ acyl is formyl, acetyl, propionyl, n-butyryl, iso-butyryl, n-valeryl, iso-valeryl, neo-valeryl, sec-valeryl, n-hexanoyl, iso-hexanoyl, neo-hexanoyl, sec-hexanoyl, n-heptanoyl, iso-heptanoyl, neo-heptanoyl, sec-heptanoyl, n-octanoyl, iso-octanoyl, neo-octanoyl, sec-octanoyl, 1-cyclopropylformyl, 1-cyclobutylformyl, 1-cyclopentylformyl, 1-cyclohexylformyl, or 1-cycloheptylcarbonyl;

the $C_2$-$C_8$ acyloxyl is acetoxyl, propionyloxyl, n-butyryloxyl, iso-butyryloxyl, n-pentanoyloxyl, iso-valeryloxyl, sec-pentanoyloxyl, neo-pentanoyloxyl, n-hexanoyloxyl, iso-hexanoyloxyl, sec-hexanoyloxyl, neo-hexanoyloxyl, n-heptanoyloxyl, iso-heptanoyloxyl, sec-heptanoyloxyl, neo-heptanoyloxyl, n-octanoyloxyl, iso-octanoyloxyl, sec-octanoyloxyl, neo-octanoyloxyl, 1-cyclopropylcarbonyloxyl, 1-cyclobutylcarbonyloxyl, 1-cyclopentylcarbonyl, 1-cyclcoheylcarbonyloxyl, or 1-cycloheptylcarbonyl;

the $C_2$-$C_8$ ester group is methoxycarbonyl, ethoxycarbonyl, propoxycarbonyl, iso-propxycarbonyl, n-butoxycarbonyl, iso-butoxycarbonyl, n-pentyloxycarbonyl, iso-pentyloxycarbonyl, neo-pentyloxycarbonyl, sec-pentyloxycarbonyl, tert-pentyloxycarbonyl, cyclopentyloxycarbonyl, n-hexyloxycarbonyl, iso-hexyloxycarbonyl, sec-hexyloxycarbonyl, neo-hexyloxycarbonyl, tert-hexyloxycarbonyl, cyclohexyloxycarbonyl, n-heptyloxycarbonyl, iso-heptyloxycarbonyl, neo-heptyloxycarbonyl, sec-heptyloxycarbonyl, tert-heptyloxycarbonyl, or cycloheptyloxycarbonyl.

The chiral bisamino-ether compound (I), as described herein, comprises a racemate, dextroisomer and laevoisomer having same chemical formula but different stereo structures and optical rotation properties.

In another aspect, the present invention provides a method of preparation of the chiral bisamino-ether compound, and the method comprises: chiral amino-methanol compound 1 (2 mmol) being reacted with a base (2-4 mmol) in an organic solvent for 5-30 minutes, and then further reacted with halogenated aryl compound 2 (1-2 mmol) at 0-160° C. for 2-96 hours to give a chiral bisamino-ether compound (I) with different substituent groups:

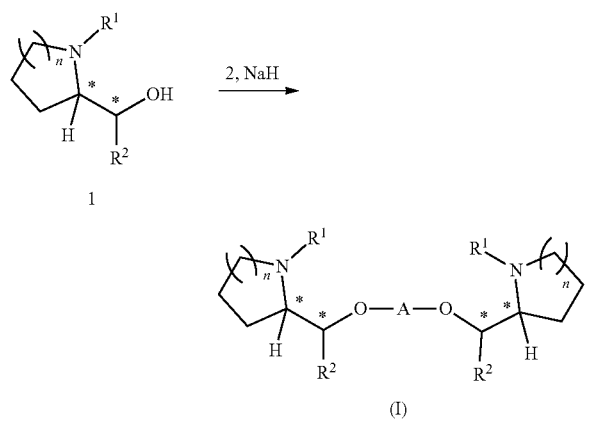

wherein: n=1 or 2; $R^1$, $R^2$, $R^3$, $R^4$, $R^5$, $R^6$ and $R^7$ are defined as in formula (I); the halogenated aryl compound 2 is selected from the group consisting of:

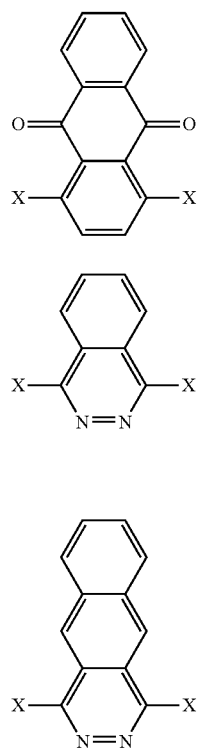

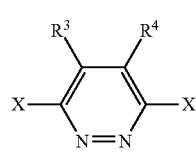

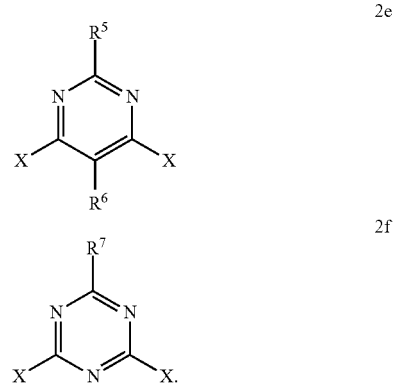

X = Cl, Br, I

In some embodiments, the organic solvent is dimethylformamide, dichloromethane, dichloroethane, tetrahydrofuran, 1,4-dioxane, toluene, xylene, trimethylbenzene, chlorobenzene, dichlorobenzene, or any combination thereof.

In some embodiments, the base is sodium hydride, potassium hydride, sodium hydroxide, potassium hydroxide, sodium carbonate, potassium carbonate, or any combination thereof.

In yet another aspect, the present invention provides a use of the chiral bisamino-ether compound, wherein the use comprises: using the chiral bisamino-ether compound I in asymmetric fluorocyclization of unsaturated heterocyclic compound 3:

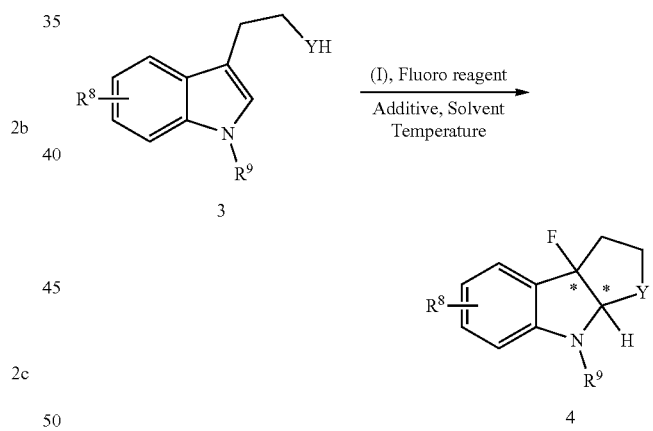

YH=NHBoc,NHTs,NHCOOBn,NHCOOMe,OH wherein: $R^8$ and $R^9$ may be the same or different, and are each independently selected from the group consisting of hydrogen, $C_1$-$C_8$ alkyl, $C_1$-$C_9$ unsaturated alkyl, halogen, haloalkyl, $C_1$-$C_8$ alkoxyl, phenyl, $C_1$-$C_8$ alkyl substituted phenyl, halophenyl, hydroxy substituted phenyl, amino substituted phenyl, di($C_1$-$C_8$ alkyl)amino substituted phenyl, $C_1$-$C_8$ alkoxy substituted phenyl, $C_1$-$C_8$ acyl substituted phenyl, ($C_1$-$C_8$ acyl)amino substituted phenyl, $C_2$-$C_8$ ester group-substituted phenyl, $C_2$-$C_8$ acyloxy substituted phenyl, or naphthyl; the fluoro reagent is bis(tetrafluoroborate) salt of 1-chloromethyl-4-fluoro-1,4-diazabicyclo[2.2.2]octane or N-fluorobisbenzenesulfonamide; and the position marked by asterisk (*) is a chiral center.

In particular, in the use, the reaction is carried out by adding the chiral bisamino-ether compound (I) and the substrate 3 into a round bottom flask, adding an additive and a solvent, adding the fluoro reagent, and then stirring the reaction at a specified temperature until the completion of the reaction.

In the use, the reaction conditions include: the solvent is acetone, acetonitrile, ethyl acetate, tetrahydrofuran, 1,4-dioxane, toluene, dichloromethane, 1,2-dichloroethane, chloroform, or a combination thereof; the chiral bisamino-ether compound (I) is in an amount of 10-120 mol %; the substrate 3 is in a concentration of 0.01-10 M; the additive is sodium hydrogencarbonate, potassium hydrogencarbonate, cesium carbonate, sodium carbonate, potassium carbonate, or a combination thereof; the reaction temperature is −78 to 40° C.; the reaction time is 2-96 hours.

In the present invention, a chiral aminomethanol compound 1 is used as a starting material to react with a halogenated aryl compound 2 in the presence of a base to obtain a substituent-containing chiral bisamino-ether compound (I). The novel chiral bisamino-ether compound (I) can be used for the asymmetric fluorocyclization of the unsaturated heterocyclic compound 3. The compounds of the invention showed some advantageous features, which include: having excellent effects with a wide range of substrates for a series of unsaturated heterocyclic compounds; having high tolerance to functional groups; having high enantioselectivity; and being able to obtain both R and S enantiomeric products with the same ee value. The above features indicate that the novel chiral bisamino-ether compound of the invention is superior over the previous bis-quinine or bis-quinidine compounds and can find broad applications in industry.

DETAILED DESCRIPTION OF EMBODIMENTS

The invention will be further understood through the following examples, which should not be construed as limiting the scope of the invention. It should be understood that all of the techniques implemented based on the above teachings of the present invention are within the scope of the present invention.

It should be noted that the abbreviations used in the examples have the following meanings: Me refers to methyl, Et refers to ethyl, Allyl refers to allyl, Ph refers to phenyl, Mes refers to 2,4,6-trimethylphenyl, Bn refers to benzyl, Ts refers to p-toluenesulfonyl, Boc refers to tert-butoxycarbonyl, NMR refers to nuclear magnetic resonance, HRMS refers to high resolution mass spectrometry, chiral HPLC refers to high performance liquid chromatography with a chiral column, ee value refers to enantiomer excess value, Selectfluor refers to 1-chloromethyl-4-fluoro-1,4-diazabicyclo[2.2.2]octane bis(tetrafluoroborate) salt, and NFSI refers to N-fluorobis benzene sulfonamide.

Example 1: Preparation of the Chiral Bisamino-Ether Compounds

In this example, the compounds obtained by the synthesis described herein are all prepared with the same process, and thus, for the sake of brevity, only the process for preparing the compound Ia is specifically described below, while the process for other subsequently listed compounds is omitted.

1,4-Bis((R)-((5)-1-methyl-2-pyrrolyl)(1-naphthyl)methoxy)phthalazine (Ia):

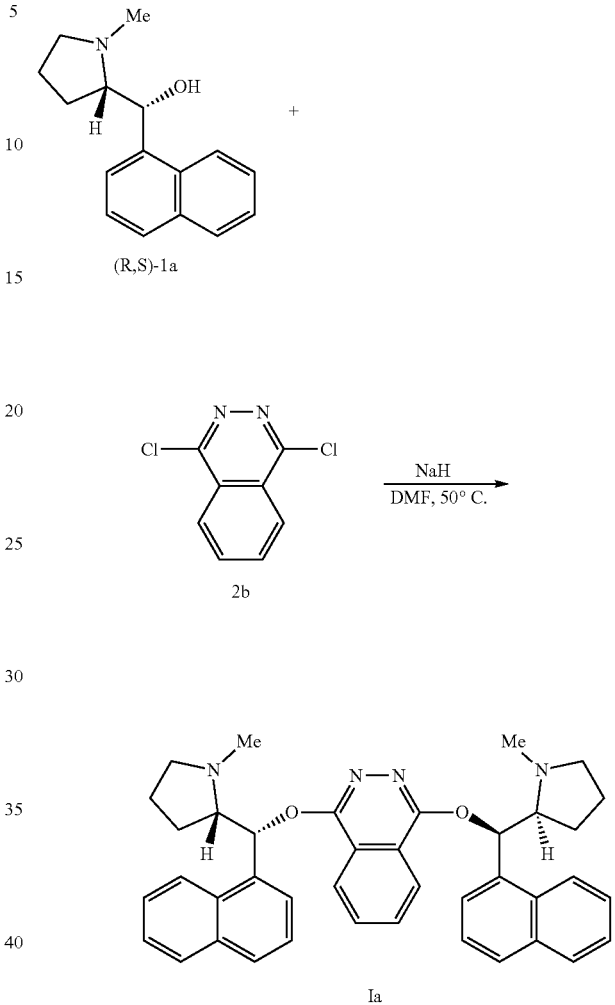

The chiral aminomethanol compound (R,S)-1a (482 mg, 2 mmol) was dissolved in dimethylformamide (6 mL), and then added with 60% sodium hydride (120 mg, 3 mmol) at room temperature for 15 min. Then, halogenated aryl compound 2b (239 mg, 1.2 mmol) was added, and the reaction was run at 50° C. in an oil bath for 24 hours. After the reaction being completed, the reaction mixture was concentrated and cooled to room temperature, and added with water (6 mL), and then was extracted with ethyl acetate (15 mL×3). The organic phase was combined and dried over anhydrous sodium sulfate, and then filtrated. The filtrate was concentrated via rotary evaporation to remove solvent. The residue was separated with silica gel column chromatography (petroleum ether/ethyl acetate=2:1, v/v) to give a light yellow solid 438 mg; mp 90-91° C.; yield 72%. $[\alpha]_D^{25}$=15.5 (c 1.0, CHCl$_3$); NMR (CDCl$_3$, 300 MHz): δ 8.45-7.33; (m, 20H), 3.15-3.10; (m, 2H), 3.03-2.98; (m, 2H), 2.51; (s, 6H), 2.45-2.24; (m, 4H), 2.02-1.93; (m, 2H), 1.78-1.58; (m, 2H); $^{13}$C NMR (CDCl$_3$, 75 MHz): δ 156.8, 135.6, 133.8, 131.9, 130.6, 128.8, 127.9, 125.9, 125.5, 125.3, 123.5, 123.2, 123.1, 122.9; HRMS (TOF$^+$) calcd. for C$_{40}$H$_{40}$N$_4$O$_2$ [M+H]$^+$609.3579, found 609.3577.

1,4-Bis((R)-((S)-1-allyl-2-pyrrolyl)(1-naphthyl)methoxy)phthalazine (Ib)

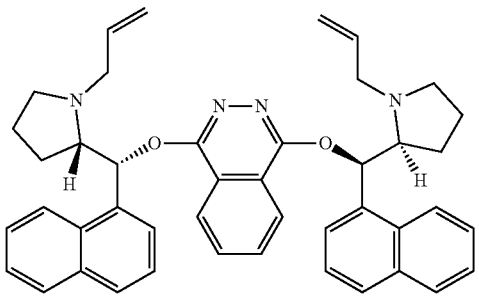

449 mg, yield 68%, light yellow solid; mp 94-95° C.; $[\alpha]_D^{25}$=18.6 (c 1.0, CHCl$_3$); $^1$H NMR (CDCl$_3$, 300 MHz): δ 7.93-7.48; (m, 16H), 6.15-6.02; (m, 2H), 5.69; (s, broad, 2H), 5.42-5.25; (m, 4H), 3.83-3.77; (m, 2H), 3.29-3.10; (m, 6H), 2.48-2.39; (m, 2H), 1.81-1.60; (m, 8H), 1.19-1.12 (m, 2H); $^{13}$C NMR (CDCl$_3$, 75 MHz): δ 136.7, 135.6, 133.6, 130.1, 129.0, 127.4, 125.7, 125.6, 125.3, 123.3, 122.6, 117.6, 67.3, 67.1, 57.0, 54.8, 24.4, 23.4; HRMS (TOF$^+$) calcd. for C$_{44}$H$_{44}$N$_4$O$_2$ [M+H]$^+$661.3534, found 661.3537.

1,4-Bis((R)-((S)-1-methyl-2-pyrrolyl)(4-trifluoromethylphenyl)methoxy)phthalazine (Ic)

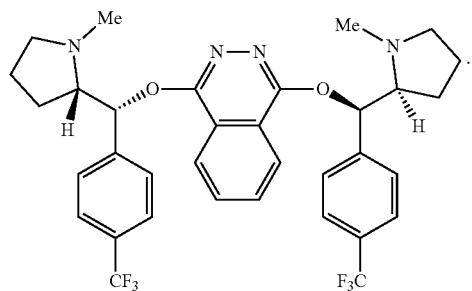

405 mg, yield 63%, light yellow solid; mp 86-87° C.; $[\alpha]_D^{25}$=24.9 (c 1.0, CHCl$_3$); $^1$H NMR (CDCl$_3$, 300 MHz): δ 8.32-6.51; (m, 14H), 3.12-3.06; (m, 2H), 2.36; (s, 6H), 2.33-2.26; (m, 2H), 2.22-2.15; (m, 2H), 1.88-1.72; (m, 6H); $^{13}$C NMR (CDCl$_3$, 75 MHz): δ 156.8, 143.8, 132.1, 129.8, 1293, 127.0, 125.2 (q, J=3.8 Hz), 123.1, 122.8, 76.1, 70.6, 57.5, 41.6, 25.9, 23.5; HRMS (TOF$^+$) calcd. for C$_{34}$H$_{34}$F$_6$N$_4$O$_2$ [M+H]$^+$645.3755, found 645.3764.

1,4-Bis((R)-(2-methoxyphenyl)((S)-1-methyl-2-pyrrolyl)methoxy)phthalazine (Id)

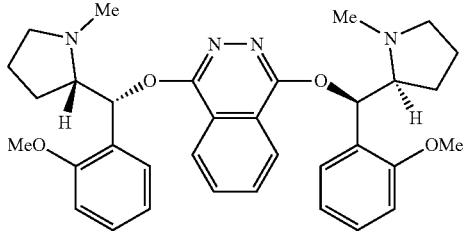

364 mg, yield 64%, light yellow solid; mp 82-83° C.; $[\alpha]_D^{25}$=25.8 (c 1.0, CHCl$_3$); $^1$H NMR (CDCl$_3$, 300 MHz): δ 8.39-6.72; (m, 14H), 3.90; (s, 6H), 3.15-3.12; (m, 2H), 3.35-3.33; (m, 2H), 2.26; (s, 6H), 1.88-1.63; (m, 8H); $^{13}$C NMR (CDCl$_3$, 75 MHz): δ 156.9, 156.6, 131.6, 128.6, 128.2, 127.2, 123.2, 122.8, 120.4, 110.7, 74.9, 68.4, 58.6, 55.6, 43.6, 28.3, 24.1; HRMS (TOF$^+$) calcd. for C$_{34}$H$_{40}$N$_4$O$_4$ [M+H]$^+$569.6761, found 569.6759.

4,6-Bis((R)-((S)-1-methyl-2-pyrrolyl)(1-naphthyl)methoxy)-2,5-diphenylpyrimidine (Ie)

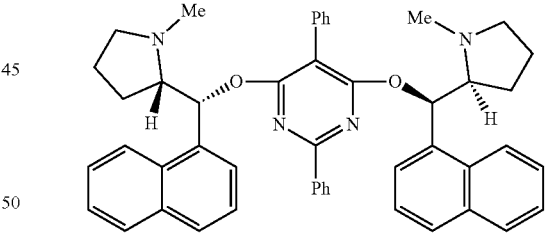

426 mg, yield 60%, light yellow solid; mp 137-138° C.; $[\alpha]_D^{25}$=17.1 (c 1.0, CHCl$_3$); $^1$H NMR (CDCl$_3$, 300 MHz): δ 8.33-7.07; (m, 26H), 3.11-3.06; (m, 2H), 2.94-2.91; (m, 2H), 2.40; (s, 6H), 2.33-2.24; (m, 2H), 2.16-2.08; (m, 2H), 1.76-1.59; (m, 6H), $^{13}$C NMR (CDCl$_3$, 75 MHz): δ 166.8, 160.6, 137.3, 136.2, 133.7, 131.8, 131.2, 130.7, 129.9, 129.0, 128.9, 128.0, 127.9, 127.6, 127.3, 126.0, 125.4, 124.1, 123.2, 104.7, 74.1, 69.3, 57.7, 41.5, 26.0, 23.1; HRMS (TOF$^+$) calcd. for C$_{48}$H$_{46}$N$_4$O$_2$ [M+H]$^+$711.4181, found 711.4183.

4,6-Bis((R)-((S)-1-allyl-2-pyrrolyl)(1-naphthyl)methoxy)-2,5-diphenylpyrimidine (If)

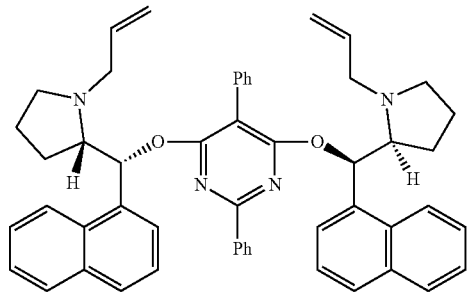

If 465.4 mg, yield 61%, light yellow solid; mp 149-150° C.; $[\alpha]_D^{25}$=17.4 (c 1.0, CHCl$_3$); $^1$H NMR (CDCl$_3$, 300 MHz): δ 8.39-7.09; (m, 26H), 5.73-5.60; (m, 2H), 5.05-4.95; (m 4H), 3.25-3.19; (m, 4H), 3.08-3.04; (m, 2H), 2.95-2.88; (m, 2H), 2.40-2.32; (m, 2H), 2.11-2.04; (m, 2H), 1.75-1.59; (m, 6H); $^{13}$C NMR (CDCl$_3$, 75 MHz): δ 159.8, 153.5, 130.2, 129.3, 126.6, 124.0, 123.9, 122.9, 121.7, 120.9, 120.7, 120.6, 120.2, 118.6, 118.3, 118.2, 117.4, 116.8, 109.2, 97.5, 68.7, 59.7, 50.8, 47.5, 19.7, 16.3; HRMS (TOF$^+$) calcd. for C$_{52}$H$_{50}$N$_4$O$_2$ [M+H]$^+$763.4007, found 763.4039.

1,4-Bis((R)-((S)-1-methyl-2-piperidinyl)(1-naphthyl)methoxy)phthalazine (Ig)

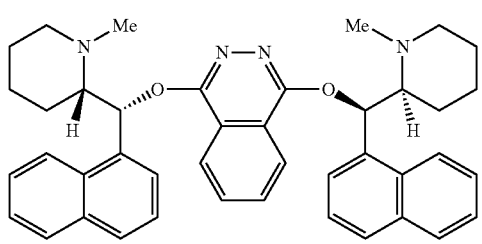

Ig 509 mg, yield 80%, light yellow solid; mp 91-92° C.; $[\alpha]_D^{25}$=15.4 (c 1.0, CHCl$_3$); $^1$H NMR (CDCl$_3$, 300 MHz): δ 8.53-7.28; (m, 20H), 3.01-2.88; (m, 3H), 2.66; (s, 6H), 2.57-2.53; (m, 2H), 2.19-2.12; (m, 2H), 2.05-1.95; (m, 1H), 1.78-1.54; (m, 6H), 1.10-0.97; (m, 2H); $^{13}$C NMR (CDCl$_3$, 75 MHz): δ 156.7, 134.9, 133.9, 132.0, 128.9, 127.9, 125.9, 125.5, 125.0, 123.8, 123.6, 123.5, 123.1, 71.7, 62.3, 58.2, 43.7, 25.8, 24.7, 24.5; HRMS (TOF$^+$) calcd. for C$_{42}$H$_{44}$N$_4$O$_2$ [M+H]$^+$637.5579, found 637.5590.

1,4-Bis((R)-((S)-1-allyl-2-piperidyl)(1-naphthyl)methoxy)phthalazine (Ih)

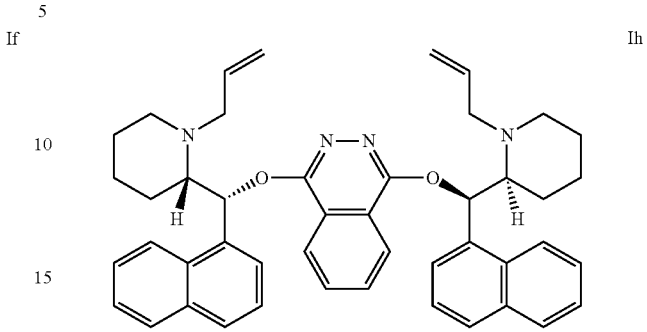

Ih 530.4 mg, yield 77%, light yellow solid; mp 96-97° C.; $[\alpha]_D^{25}$=22.7 (c 1.0, CHCl$_3$); $^1$H NMR (CDCl$_3$, 300 MHz): δ 8.53-7.36; (m, 20H), 5.80-5.67; (m, 2H), 5.12-4.92; (m 4H), 3.92-3.86; (m, 2H), 3.26-2.94; (m, 6H), 2.26-2.20; (m, 2H), 2.05-1.97; (m, 2H), 1.82-1.78; (m, 2H), 1.66-1.49; (m, 6H), 1.22-1.05; (m, 2H); $^{13}$C NMR (CDCl$_3$, 75 MHz): δ 156.7, 135.4, 133.9, 131.9, 130.6, 128.8, 127.9, 125.9, 125.5, 125.0, 124.1, 124.0, 123.5, 123.1, 117.6, 72.4, 64.0, 56.9, 52.3, 25.2, 24.9, 24.2; HRMS (TOF$^+$) calcd. for C$_{46}$H$_{48}$N$_4$O$_2$ [M+H]$^+$689.6225, found 689.6237.

3,6-Bis((R)-((S)-1-methyl-2-piperidinyl)(1-naphthyl)methoxy)pyridazine (Ii)

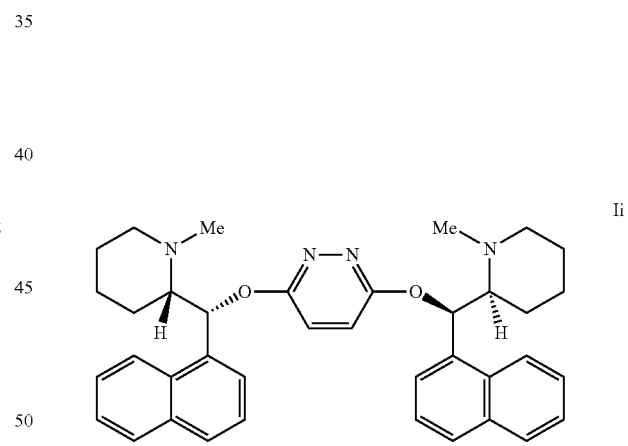

Ii 433.9 mg, yield 74%, light yellow solid; mp 85-86° C.; $[\alpha]_D^{25}$=10.0 (c 1.0, CHCl$_3$); $^1$H NMR (CDCl$_3$, 300 MHz): δ 8.12-7.28; (m, 20H), 3.73-3.65; (m, 1H), 3.17-3.13; (m, 2H), 2.75; (s, 6H), 2.61-2.58; (m, 2H), 2.32-2.24; (m, 2H), 1.94-1.86; (m, 2H), 1.77-1.47; (m, 8H), 1.10-0.98; (m, 2H); $^{13}$C NMR (CDCl$_3$, 75 MHz): δ 163.6, 151.2, 133.9, 133.2, 130.8, 130.3, 129.1, 128.4, 126.5, 124.9, 124.1, 122.8, 121.2, 72.8, 66.8, 53.1, 43.1, 25.3, 24.4, 24.1; HRMS (TOF$^+$) calcd. for C$_{38}$H$_{42}$N$_4$O$_2$ [M+H]$^+$587.7352, found 587.7361.

4,6-Bis((R)-((S)-1-methyl-2-piperidyl)(1-naphthyl)methoxy)-2,5-diphenylpyrimidine (Ij)

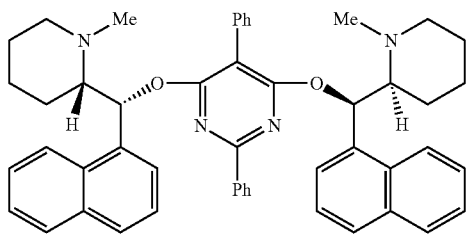

450 mg, yield 61%, light yellow solid; mp 150-151° C.; $[\alpha]_D^{25}$=24.3 (c 1.0, CHCl$_3$); $^1$H NMR (CDCl$_3$, 300 MHz): δ 8.32-7.02; (m, 27H), 3.05-3.01; (m, 2H), 2.64-2.61; (m, 2H), 2.39-2.27; (m, 2H), 1.78-1.47; (m, 10H), 1.11-0.96; (m, 2H), $^{13}$C NMR (CDCl$_3$, 75 MHz): δ 176.1, 166.6, 160.6, 136.9, 135.0, 133.7, 131.4, 130.3, 130.1, 129.1, 127.9, 127.8, 127.6, 126.3, 125.5, 125.1, 124.6, 122.9, 104.9, 72.7, 66.0, 56.9, 24.6, 23.7, 23.3, 22.6; HRMS (TOF$^+$) calcd. for C$_{50}$H$_{50}$N$_4$O$_2$ [M+H]$^+$739.4007, found 739.3988.

2-Methyl-4,6-bis((R)-((S)-1-methyl-2-piperidinyl)(1-naphthyl)methoxy)pyrimidine (Ik)

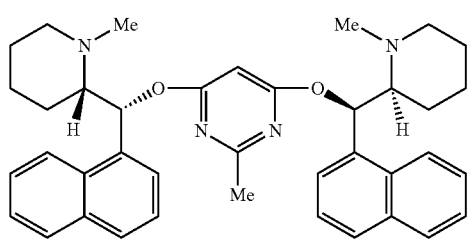

456 mg, yield 76%, light yellow solid; mp 85-86° C.; $[\alpha]_D^{25}$=16.3 (c 1.0, CHCl$_3$); $^1$H NMR (CDCl$_3$, 300 MHz): δ 8.12-7.38; (m, 16H), 6.32; (s, 1H), 3.04-2.97; (m, 2H), 2.67; (s, 6H), 2.22-2.12; (m, 2H), 2.04; (s, 3H), 1.90-1.52; (m, 7H), 1.40-1.36; (m, 2H), 1.01-0.92; (m, 2H); $^{13}$C NMR (CDCl$_3$, 75 MHz): δ 170.3, 166.9, 134.7, 133.7, 130.2, 129.0, 127.8, 126.1, 125.4, 126.3, 124.7, 123.0, 90.6, 71.4, 66.7, 58.2, 43.2, 25.8, 24.6, 24.3; HRMS (TOF$^+$) calcd. for C$_{39}$H$_{44}$N$_4$O$_2$ [M+H]$^+$601.3537, found 601.3530.

1,4-Bis((R)-(1-naphthyl)((S)-1-propyl-2-piperidyl)methoxy)phthalazine (Il)

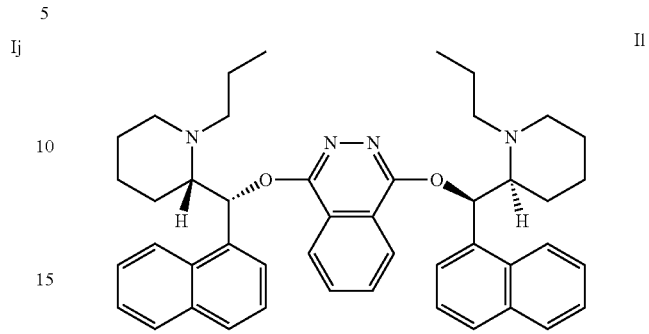

505 mg, yield 73%, light yellow solid; mp 100-101° C.; $[\alpha]_D^{25}$=21.4 (c 1.0, CHCl$_3$); $^1$H NMR (CDCl$_3$, 300 MHz): δ 8.50-7.33; (m, 20H), 3.19-3.07; (m, 4H), 2.90-2.87; (m, 2H), 2.47-2.38; (m, 2H), 2.18-1.94; (m, 41H), 1.81-1.75; (m, 2H), 1.64-1.50; (m, 6H), 1.42-1.08; (m, 4H), 0.52; (t, J=9.0 Hz, 6H); $^{13}$C NMR (CDCl$_3$, 75 MHz): δ 156.6, 135.6, 133.9, 131.9, 130.6, 128.8, 127.7, 125.8, 125.4, 125.0, 124.1, 124.0, 123.0, 72.6, 64.4, 55.3, 52.5, 25.1, 24.8, 24.1, 20.0, 11.6; HRMS (TOF$^+$) calcd. for C$_{46}$H$_{52}$N$_4$O$_2$ [M+H]$^+$ 693.6384, found 693.6391.

4,6-Bis((R)-((S)-1-allyl-2-piperidyl)(1-naphthyl)methoxy)-2-methylpyrimidine (Im)

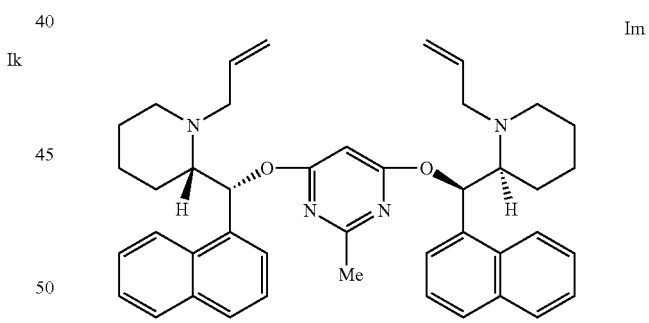

515 mg, yield 79%, light yellow solid; mp 97-98° C.; $[\alpha]_D^{25}$=18.6 (c 1.0, CHCl$_3$); $^1$H NMR (CDCl$_3$, 300 MHz): δ 8.23-7.43; (m, 16H), 6.20-6.06; (m, 2H), 5.44-5.30; (m 4H), 3.81-3.75; (m, 2H), 3.50-3.42; (m, 2H), 3.14-3.10; (m, 2H), 2.83-2.79; (m, 2H), 2.41-2.33; (m, 2H), 2.15; (s, 3H), 1.92-1.61; (m, 8H), 1.39-1.32; (m, 3H), 1.10-0.89; (m, 3H); $^{13}$C NMR (CDCl$_3$, 75 MHz): δ 170.4, 167.0, 135.2, 133.7, 130.5, 128.9, 127.8, 125.9, 125.4, 125.3, 123.5, 118.2, 90.8, 71.8, 63.0, 57.1, 53.4, 25.9, 25.6, 25.3, 24.3; HRMS (TOF$^+$) calcd. for C$_{43}$H$_{48}$N$_4$O$_2$ [M+H]$^+$653.4977, found 653.4980.

3,6-Bis((R)-((S)-1-allyl-2-piperidyl)(1-naphthyl)methoxy)pyridazine (In)

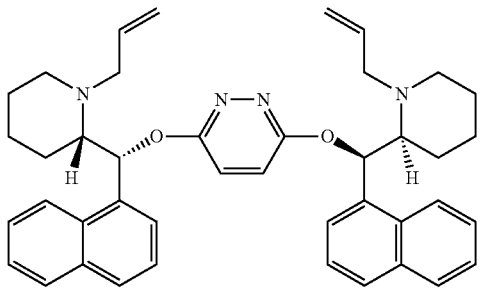

440 mg, yield 69%, brown oil; $[\alpha]_D^{25}$=42.7 (c 1.0, CHCl$_3$); $^1$H NMR (CDCl$_3$, 300 MHz): δ 8.21-7.23; (m, 16H), 6.15-6.02; (m, 2H), 5.46-5.31; (m 4H), 3.86-3.79; (m, 2H), 3.48-3.41; (m, 2H), 3.16-3.12; (m, 2H), 2.89-2.85; (m, 2H), 2.41-2.32; (m, 2H), 21.90-1.61; (m, 9H), 1.48-1.43; (m, 3H), 1.13-1.00; (m, 2H); $^{13}$C NMR (CDCl$_3$, 75 MHz): δ 163.7, 151.1, 133.8, 130.7, 130.6, 131.0, 129.0, 128.2, 126.2, 125.7, 124.9, 124.3, 123.3, 121.1, 73.4, 63.1, 57.2, 53.5, 25.4, 25.1, 24.1; HRMS (TOF$^+$) calcd. for C$_{42}$H$_{46}$N$_4$O$_2$ [M+H]$^+$639.5690, found 639.5692.

1,4-Bis((S)-((S)-1-methyl-2-pyrrolyl)(phenypmethoxy)phthalazine (Io)

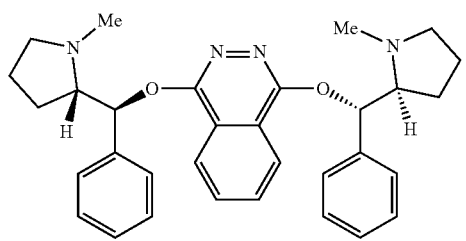

396 mg, yield 78%, light yellow solid; mp 81-82° C.; $[\alpha]_D^{25}$=-40.6 (c 1.0, CHCl$_3$); $^1$H NMR (CDCl$_3$, 300 MHz): δ 8.29-6.37; (m, 16H), 3.12-3.02; (m, 4H), 2.52; (s, 6H), 2.40-2.32; (m, 2H), 1.71-1.64; (m, 8H); $^{13}$C NMR (CDCl$_3$, 75 MHz): δ 156.5, 139.5, 131.7, 127.9, 127.6, 123.0, 122.8, 80.0, 69.2, 58.1, 43.1, 28.3, 23.4; HRMS (TOF$^+$) calcd. for C$_{32}$H$_{36}$N$_4$O$_2$ [M+H]$^+$509.4573, found 509.4576.

1,4-Bis((S)-((S)-1-methyl-2-pyrrolyl)(1-naphthyl)methoxy)phthalazine (Ip)

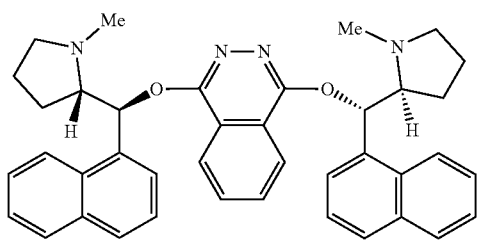

389 mg, yield 64%, light yellow solid; mp 89-90° C.; $[\alpha]_D^{25}$=-32.1 (c 1.0, CHCl$_3$); $^1$H NMR (CDCl$_3$, 300 MHz): δ 8.54-6.99; (m, 20H), 3.35-3.28; (m, 2H), 3.13-3.08; (m, 2H), 2.36-2.30; (m, 6H), 2.27; (s, 614), 1.86-1.69; (m, 2H), 1.64-1.60; (m, 6H); $^{13}$C NMR (CDCl$_3$, 75 MHz): δ 156.7, 135.9, 133.9, 131.7, 131.3, 128.7, 128.1, 125.8, 125.6, 125.3, 125.2, 124.7, 123.1, 122.8, 79.1, 69.0, 58.5, 43.6, 29.2, 23.9; HRMS (TOF$^+$) calcd. for C$_{40}$H$_{40}$N$_4$O$_2$ [M+H]$^+$ 609.3579, found 609.3576.

1,4-Bis((S)-((S)-1-allyl-2-pyrrolyl)(1-naphthyl)methoxy)phthalazine (Iq)

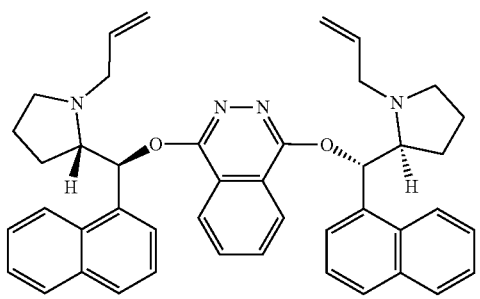

437 mg, yield 66%, light yellow solid; mp. 93-94° C.; $[\alpha]_D^{25}$=-20.7 (c 1.0, CHCl$_3$); $^1$H NMR (CDCl$_3$, 300 MHz): δ 8.47-7.28; (m, 16H), 5.81-5.68; (m, 2H), 4.99-4.93; (m, 4H), 3.77-3.62; (m, 2H), 3.1-3.24; (m, 4H), 3.01-2.95; (m, 2H), 2.57-2.45; (m, 2H), 1.82-1.64; (m, 10H), 1.30-1.26; (m, 2H); $^{13}$C NMR (CDCl$_3$, 75 MHz): δ 156.9, 133.7, 131.9, 131.0, 128.6, 128.2, 125.8, 125.3, 125.2, 124.4, 123.2, 122.8, 66.7, 59.1, 54.5, 29.7, 28.9, 24.2; HRMS (TOF$^+$) calcd. for C$_{44}$H$_{44}$N$_4$O$_2$ [M+H]$^+$661.3534, found 661.3532.

1,4-Bis((S)-((S)-1-methyl-2-pyrrolyl)(4-trifluoromethylphenyl)methoxy)phthalazine (Ir)

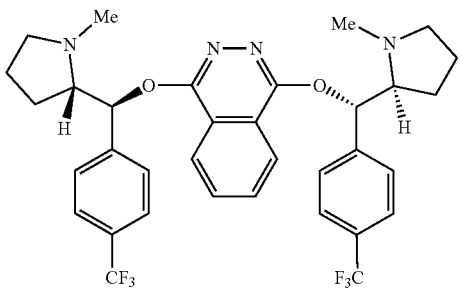

418.6 mg, yield 65%, light yellow solid; mp 88-89° C.; $[\alpha]_D^{25}$=-19.3 (c 1.0, CHCl$_3$); $^1$H NMR (CDCl$_3$, 300 MHz): δ 8.31-6.39; (m, 14H), 3.09-3.00; (m, 4H), 2.51; (s, 6H), 2.37-2.29; (m, 2H), 1.77-1.49; (m, 8H); $^{13}$C NMR (CDCl$_3$, 75 MHz): δ 156.5, 143.3, 132.1, 130.2, 129.8, 129.3, 128.9, 127.8, 124.8, 122.9, 122.6, 124.8 (q, J=3.8 Hz), 122.9, 122.6, 79.3, 68.9, 57.9, 42.9, 27.9, 23.6; HRMS (TOF$^+$) calcd. for C$_{34}$H$_{34}$F$_6$N$_4$O$_2$ [M+H]$^+$645.3755, found 645.3761.

17

4,6-bis((S)-((S)-1-methyl-2-pyrrolyl)(1-naphthyl)methoxy)-2,5-diphenylpyrimidine (Is)

18

1,4-Bis((S)-((S)-1-methyl-2-piperidinyl)(1-naphthyl)methoxy)phthalazine (Iu)

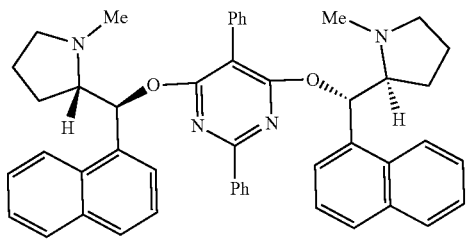

433 mg, yield 61%, light yellow solid; mp 136-137° C.; $[\alpha]_D^{25}=-23.6$ (c 1.0, CHCl$_3$); $^1$H NMR (CDCl$_3$, 300 MHz): δ 8.50-6.76; (m, 26H), 3.22-3.08; (m, 2H), 2.38-2.30; (m, 2H), 2.26; (s, 6H), 1.86-1.77; (m, 2H), 1.65-1.53; (m, 4H), 1.43-1.38; (m, 2H); $^{13}$C NMR (CDCl$_3$, 75 MHz): δ 167.0, 162.7, 159.3, 136.1, 133.9, 132.5, 131.3, 131.0, 130.2, 129.0, 128.7, 128.5, 128.4, 128.3, 128.1, 126.2, 125.3, 124.5, 118.9, 81.6, 69.5, 58.4, 43.2, 28.6, 23.5; HRMS (TOF$^+$) calcd. for C$_{48}$H$_{46}$N$_4$O$_2$ [M+H]$^+$ 711.4181, found 711.4186.

477 mg, yield 75%, light yellow solid; mp. 93-94° C.; $[\alpha]_D^{25}=-36.9$ (c 1.0, CHCl$_3$); $^1$H NMR (CDCl$_3$, 300 MHz): δ 8.66-7.11; (m, 20H), 3.41-3.35; (m, 2H), 2.95-2.91; (m, 2H), 2.43; (s, 6H), 2.49-2.39; (m, 2H), 1.56-1.51; (m, 6H), 1.18-1.03; (m, 6H); $^{13}$C NMR (CDCl$_3$, 75 MHz): δ 156.1, 135.7, 134.0, 131.8, 131.6, 128.7, 128.4, 127.1, 125.9, 125.4, 125.3, 123.1, 122.8, 78.4, 66.3, 55.6, 42.9, 27.3, 24.2, 23.5; HRMS (TOF$^+$) calcd. for C$_{42}$H$_{44}$N$_4$O$_2$ [M+H]$^+$ 637.5579, found 637.5584.

4,6-bis((S)-((S)-1-allyl-2-pyrrolyl)(1-naphthyl)methoxy)-2,5-diphenylpyrimidine (It)

4,6-Bis((S)-((5)-1-methyl-2-piperidyl)(1-naphthyl)methoxy)-2,5-diphenylpyrimidine (Iv)

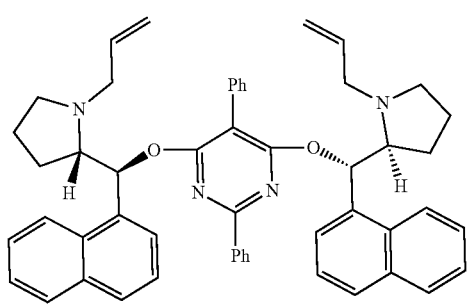

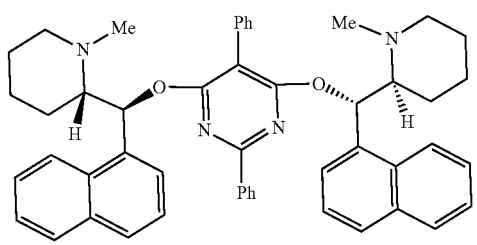

480 mg, yield 63%, light yellow solid; mp 147-148° C.; $[\alpha]_D^{25}=-65.3$ (c 1.0, CHCl$_3$); $^1$H NMR (CDCl$_3$, 300 MHz): δ 8.58-6.71; (m, 26H), 5.84-5.70; (m, 2H), 5.04-4.96; (m, 4H), 3.44-3.33; (m, 4H), 3.11-3.06; (m, 2H), 2.93-2.86; (m, 2H), 2.44-2.36; (m, 2H), 1.79-1.69; (m, 2H), 1.60-1.40; (m, 6H); $^{13}$C NMR (CDCl$_3$, 75 MHz): δ 166.8, 161.2, 137.6, 137.1, 136.2, 133.9, 132.4, 131.6, 131.0, 129.0, 128.3, 128.0, 127.6, 125.8, 125.3, 124.9, 116.4, 104.6, 80.5, 66.8, 59.1, 54.5, 28.5, 24.0; HRMS (TOF$^+$) calcd. for C$_{52}$H$_{50}$N$_4$O$_2$ [M+H]$^+$ 763.4007, found 763.4038.

472 mg, yield 64%, light yellow solid; mp 150-151° C.; $[\alpha]_D^{25}=-17.0$ (c 1.0, CHCl$_3$); $^1$H NMR (CDCl$_3$, 300 MHz): δ 8.40-7.10; (m, 26H), 3.67-3.56; (m, 1H), 3.06-2.88; (m, 3H), 3.00; (s, 3H), 2.94; (s, 3H), 2.42-2.30; (m, 2H), 1.67-1.48; (m, 5H), 1.28-0.86; (m, 5H); $^{13}$C NMR (CDCl$_3$, 75 MHz): δ 165.5, 164.3, 162.7, 154.7, 133.7, 132.4, 132.0, 131.3, 131.0, 130.8, 130.4, 128.9, 128.8, 128.5, 128.1, 128.0, 127.9, 127.6, 127.3, 126.2, 125.7, 125.3, 124.9, 105.9, 67.4, 56.9, 43.9, 36.5, 31.5, 27.8, 24.5, 23.6; HRMS (TOF$^+$) calcd. for C$_{50}$H$_{50}$N$_4$O$_2$ [M+H]$^+$ 739.4007, found 739.4005.

1,4-Bis((S)-((S)-1-methyl-2-piperidyl)(1-naphthyl)methoxy)-9,10-nonanedione (Iw)

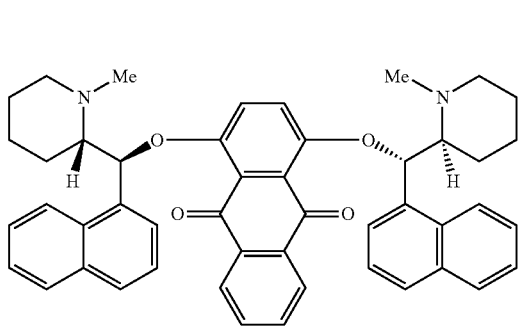

407 mg, yield 57%, brown solid; mp 149-148° C.; [α]$_D^{25}$=−39.1 (c 1.0, CHCl$_3$); $^1$H NMR (CDCl$_3$, 300 MHz): δ 8.66-6.80; (m, 22H), 3.63-3.55; (m, 2H), 3.29-3.25; (m, 1H), 2.80-2.70; (m, 2H), 2.06; (s, 6H), 1.92-1.37; (m, 8H), 1.21-0.95; (m, 3H); $^{13}$C NMR (CDCl$_3$, 75 MHz): δ 182.6, 182.1, 176.8, 155.8, 138.5, 134.2, 134.0, 133.9, 133.6, 133.0, 131.5, 131.4, 129.6, 129.1, 127.3, 126.8, 126.4, 126.3, 125.5, 123.9, 123.8, 120.7, 69.2, 57.6, 43.8, 27.5, 23.9, 23.4, 22.9; HRMS (TOF$^+$) calcd. for C$_{48}$H$_{46}$N$_2$O$_4$ [M+H]$^+$715.5179, found 715.5172.

1,4-Bis((R)-((R)-1-allyl-2-piperidyl)(1-naphthyl)methoxy)phthalazine (Ix)

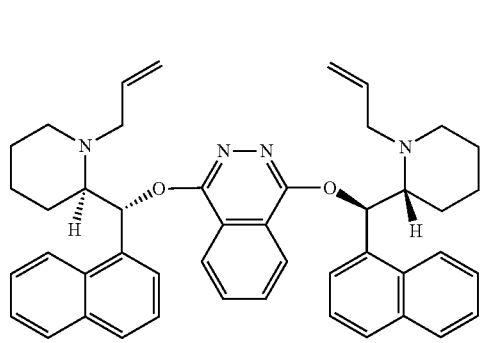

523.6 mg, yield 76%, light yellow solid; mp 97-98° C.; [α]$_D^{25}$=−23.9 (c 1.0, CHCl$_3$); $^1$H NMR (CDCl$_3$, 400 MHz): δ 8.53-7.32; (m, 20H), 6.09-5.99; (m, 2H), 5.42-5.25; (m 4H), 3.98-3.93; (m, 2H), 3.53-3.50; (m, 2H), 3.20-3.04; (m, 4H), 2.41-2.35; (m, 2H), 2.13-2.05; (m, 2H), 1.86-1.82; (m, 2H), 1.64-1.59; (m, 4H), 1.21-1.12; (m, 3H), 0.91-0.87; (m, 3H); $^{13}$C NMR (CDCl$_3$, 100 MHz): δ 157.8, 156.5, 133.9, 131.9, 131.8, 130.7, 128.8, 128.0, 126.0, 125.5, 125.0, 124.1, 123.8, 123.5, 123.2, 122.8, 122.6, 72.2, 63.7, 62.8, 56.9, 53.0, 24.9, 24.1; HRMS (TOF$^+$) calcd. for C$_{46}$H$_{48}$N$_4$O$_2$ [M+H]$^+$689.6225, found 689.6231.

1,4-Bis((S)-((R)-1-allyl-2-piperidyl)(1-naphthyl)methoxy)phthalazine (Iy)

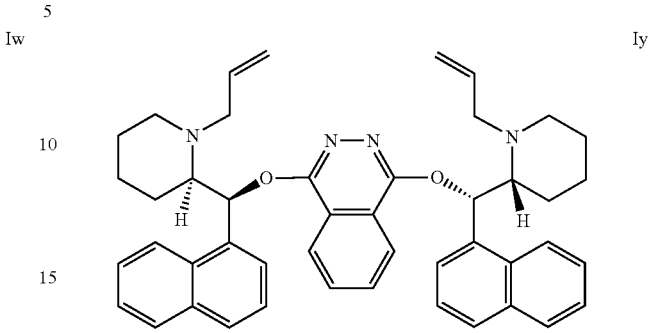

523.6 mg, yield 76%, light yellow solid; mp 96-97° C.; [α]$_D^{25}$=45.3 (c 1.0, CHCl$_3$); $^1$H NMR (CDCl$_3$, 400 MHz): δ 8.53-7.32; (m, 20H), 6.09-5.99; (m, 2H), 5.42-5.25; (m 4H), 3.98-3.93; (m, 2H), 3.53-3.50; (m, 2H), 3.20-3.04; (m, 4H), 2.41-2.35; (m, 2H), 2.13-2.05; (m, 2H), 1.86-1.82; (m, 2H), 1.64-1.59; (m, 4H), 1.21-1.12; (m, 3H), 0.91-0.87; (m, 3H); $^{13}$C NMR (CDCl$_3$, 100 MHz): δ 157.8, 156.5, 133.9, 131.9, 131.8, 130.7, 128.8, 128.0, 126.0, 125.5, 125.0, 124.1, 123.8, 123.5, 123.2, 122.8, 122.6, 72.2, 63.7, 62.8, 56.9, 53.0, 24.9, 24.1; HRMS (TOF$^+$) calcd. for C$_{46}$H$_{48}$N$_4$O$_2$ [M+H]$^+$689.6225, found 689.6231.

Example 2: Different Chiral Bisamino-ether Compounds Used for Asymmetric Fluorocyclization of 3a

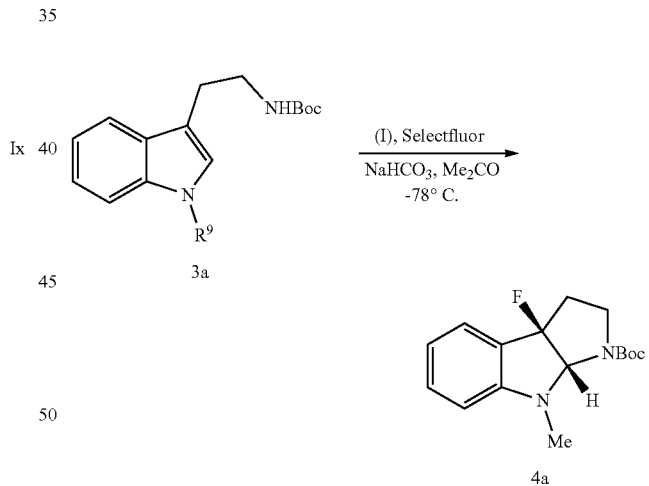

In a 10 mL round-bottom flask were added 3a (27.6 mg, 0.1 mmol), sodium bicarbonate (NaHCO$_3$, 10.1 mg, 0.12 mmol), chiral bisamino-ether compound I (0.12 mmol) and 2.5 mL of acetone, and the mixture was stirred at −78° C. for 15 minutes. Then, a bis(tetrafluoroborate) salt of 1-4-fluoro-1,4-diazabicyclo[2.2.2]octane (Selectfluor, 42.5 mg, 0.12 mmol) was added. After the reaction being completed, the reaction mixture was concentrated by rotary evaporation at room temperature, and then water (1 mL) was added. The mixture was extracted with ethyl acetate (5 mL×3), and the organic phases were combined and dried over anhydrous sodium sulfate. After filtration, the filtrate was concentrated by rotary evaporation to remove solvent. The residue was separated with silica gel column chromatography (petroleum ether/ethyl acetate=6:1, v/v) to give 4a. The ee value was analyzed by chiral HPLC, and the experimental results are shown in Table 1.

TABLE 1

Different Chiral Bisamino-ether Compounds Used for Asymmetric Fluorocyclization of 3a

| I | Reaction time (h) | Yield (%) | ee value (%) |
|---|---|---|---|
| Ia | 48 | 59 | 13 |
| Ig | 48 | 75 | 86 |
| In | 48 | 46 | −22 |
| Ih | 48 | 80 | 93 |
| If | 72 | 55 | 14 |
| Il | 48 | 65 | 79 |
| In | 48 | 60 | 19 |
| Ik | 48 | 55 | 26 |

Example 3: Different Solvents Used for Asymmetric Fluorocyclization of 3a

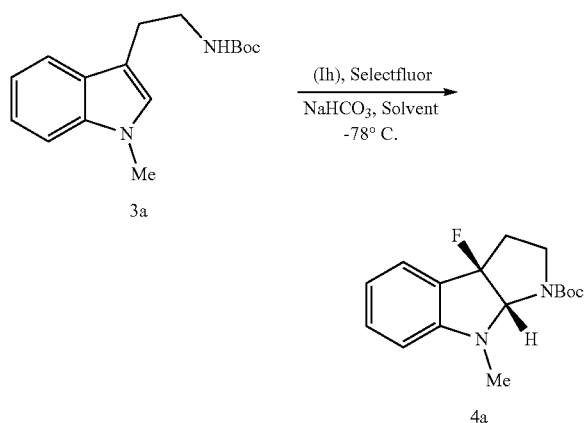

3a

4a

In a 10 mL round-bottom flask were added 3a (27.6 mg, 0.1 mmol), NaHCO₃ (10.1 mg, 0.12 mmol), chiral bisamino-ether compound Ih (82.6 mg, 0.12 mmol) and a solvent (2.5 mL), and the mixture was stirred at −78° C. for 15 minutes. Then, Selectfluor (42.5 mg, 0.12 mmol) was added. After the reaction being completed, the reaction mixture was concentrated by rotary evaporation at room temperature, and then water (1 mL) was added. The mixture was extracted with ethyl acetate (5 mL×3), and the organic phases were combined and dried over anhydrous sodium sulfate. After filtration, the filtrate was concentrated by rotary evaporation to remove solvent. The residue was separated with silica gel column chromatography (petroleum ether/ethyl acetate=6:1, v/v) to give 4a. The ee value was analyzed by chiral HPLC, and the experimental results are shown in Table 2.

TABLE 2

Different Solvents for Asymmetric Fluorocyclization of 3a

| Solvent | Reaction time (h) | Yield (%) | ee value (%) |
|---|---|---|---|
| Me₂CO | 48 | 80 | 93 |
| MeOH | 48 | 55 | 33 |
| PhMe | 96 | <5 | — |
| MeCN | 48 | 47 | 51 |
| EtOAc | 96 | <5 | — |
| THF | 72 | 50 | 48 |
| CH₂Cl₂ | 96 | <5 | — |

Example 4: Different Additives for Asymmetric Fluorocyclization of 3a

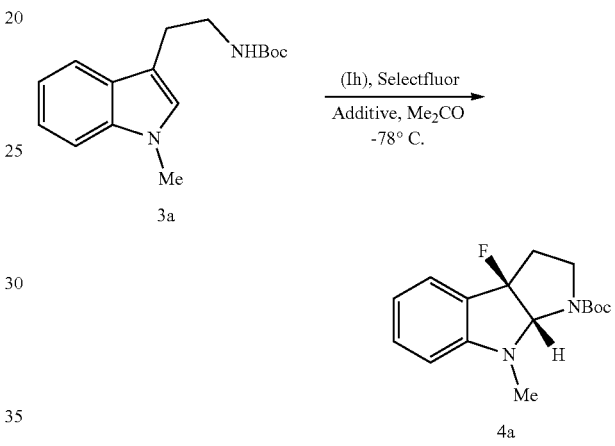

3a

4a

In a 10 mL round-bottom flask were added 3a (27.6 mg, 0.1 mmol), an additive (0.12 mmol), chiral bisamino-ether compound Ih (82.6 mg, 0.12 mmol), and acetone (2.5 mL), and the mixture was stirred at −78° C. for 15 minutes. Then, Selectfluor (42.5 mg, 0.12 mmol) was added. After the reaction being completed, the reaction mixture was concentrated by rotary evaporation room temperature, and then water (1 mL) was added. The mixture was extracted with ethyl acetate (5 mL×3), and the organic phases were combined and dried over anhydrous sodium sulfate. After filtration, the filtrate was concentrated by rotary evaporation to remove solvent. The residue was separated with silica gel column chromatography (petroleum ether/ethyl acetate=6:1, v/v) to give 4a. The ee value was analyzed by chiral HPLC, and the experimental results are shown in Table 3.

TABLE 3

Different Additives for Asymmetric Fluorocyclization of 3a

| Additive | Reaction time (h) | Yield (%) | ee value (%) |
|---|---|---|---|
| NaHCO₃ | 48 | 80 | 93 |
| KHCO₃ | 48 | 76 | 88 |
| Na₂CO₃ | 48 | 71 | 87 |
| K₂CO₃ | 48 | 64 | 83 |
| Cs₂CO₃ | 48 | 57 | 79 |

Example 5: Different Temperatures for Asymmetric fluorocyclization of 3a

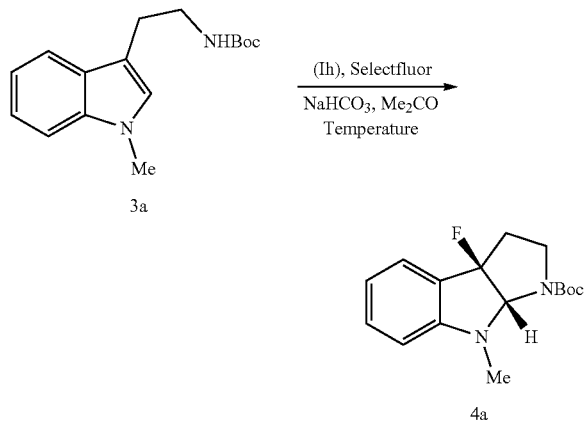

In a 10 mL round-bottom flask were added 3a (27.6 mg, 0.1 mmol), NaHCO₃ (10.1 mg, 0.12 mmol), chiral bisamino-ether compound Ih (82.6 mg, 0.12 mmol), and acetone (2.5 mL), and the mixture was stirred at different temperatures for 15 minutes. Then, Selectfluor (42.5 mg, 0.12 mmol) was added. After the reaction being completed, the reaction mixture was concentrated by rotary evaporation at room temperature, and then water (1 mL) was added. The mixture was extracted with ethyl acetate (5 mL×3), and the organic phases were combined and dried over anhydrous sodium sulfate. After filtration, the filtrate was concentrated by rotary evaporation to remove solvent. The residue was separated with silica gel column chromatography (petroleum ether/ethyl acetate=6:1, v/v) to give 4a. The ee value was analyzed by chiral HPLC, and the experimental results are shown in Table 4:

TABLE 4

Different Temperatures for Asymmetric Fluorocyclization of 3a

| Temperature (° C.) | Reaction time (h) | Yield (%) | ee value (%) |
|---|---|---|---|
| −78 | 48 | 80 | 93 |
| −40 | 24 | 65 | 45 |
| −20 | 24 | 54 | 37 |
| 0 | 12 | 55 | 30 |

Example 6: Chiral Bisamino-Ether Compound Ih for Catalytic Enantioselective Fluorocyclization of 3a

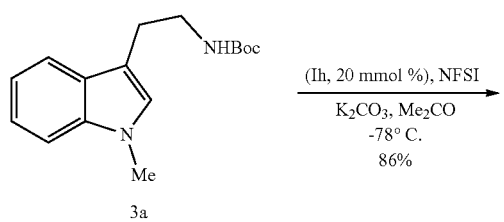

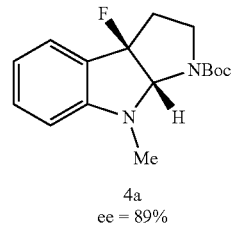

4a
ee = 89%

In a 10 mL round-bottom flask were added 3a (27.6 mg, 0.1 mmol), K₂CO₃ (20.7 mg, 0.15 mmol), chiral bisamino-ether compound Ih (13.8 mg, 0.02 mmol) and acetone (1 mL), and the mixture was stirred at −78° C. for 15 minutes. Then, N-fluorobisbenzenesulfonamide (NFSI, 37.8 mg, 0.12 mmol) was added and reacted for 72 hours. The reaction mixture was concentrated by rotary evaporation at room temperature, and then water (1 mL) was added. The mixture was extracted with ethyl acetate (5 mL×3), and the organic phases were combined and dried over anhydrous sodium sulfate. After filtration, the filtrate was concentrated by rotary evaporation to remove solvent. The residue was separated with silica gel column chromatography (petroleum ether/ethyl acetate=6:1, v/v) to give 25.1 mg of 4a, with yield of 86% and ee value of 89% as analyzed with chiral HPLC.

Example 7: Asymmetric Fluorocyclization of the Substrate 3a-s

In a 10 mL round-bottom flask were added 3 (0.1 mmol), sodium bicarbonate (NaHCO₃, 10.1 mg, 0.12 mmol), chiral bisamino-ether compound Ih (82.6 mg, 0.12 mmol) and acetone (2.5 mL), and the mixture was stirred at −78° C. for 15 minutes. Then a bis(tetrafluoroborate) salt of 1-chloromethyl-4-fluoro-1,4-diazabicyclo[2.2.2]octane (Selectfluor, 42.5 mg, 0.12 mmol) was added. After the reaction being completed, the reaction mixture was concentrated by rotary evaporation at room temperature, and then water (1 mL) was added. The mixture was extracted with ethyl acetate (5 mL×3), and the organic phases were combined and dried over anhydrous sodium sulfate. After filtration, the filtrate was concentrated by rotary evaporation to remove solvent. The residue was separated with silica gel column chromatography (petroleum ether/ethyl acetate=6:1, v/v) to give 4. The ee value was analyzed by chiral HPLC, and the experimental results are shown in Table 7.

Example 8: Asymmetric Fluorocyclization of the Substrate 3aa-an

In a 10 mL round-bottom flask were added 3 (0.1 mmol), sodium bicarbonate (NaHCO₃, 10.1 mg, 0.12 mmol), chiral bisamino-ether compound Ig (76.3 mg, 0.12 mmol) and acetone (2.5 mL), and the mixture was stirred at −78° C. for 15 minutes. Then a bis(tetrafluoroborate) salt of 1-chloromethyl-4-fluoro-1,4-diazabicyclo[2.2.2]octane (Selectfluor, 42.5 mg, 0.12 mmol) was added. After the reaction being completed, the reaction mixture was concentrated by rotary evaporation at room temperature, and then water (1 mL) was added. The mixture was extracted with ethyl acetate (5 mL×3), and the organic phases were combined and dried over anhydrous sodium sulfate. After filtration, the filtrate was concentrated by rotary evaporation to remove solvent. The residue was separated with silica gel column chromatography (petroleum ether/ethyl acetate=6:1, v/v) to give 4. The ee value was analyzed by chiral HPLC, and the experimental results are shown in Table 7.

TABLE 7

Results of Asymmetric Fluorocyclization for Substrate 3

| Substrate 3 | | Product 4 | | Reaction time (h) | Yield (%) | ee value (%) |
|---|---|---|---|---|---|---|
| (indole with NHBoc tether, N-Me) | 3a | (fluorinated pyrroloindoline, N-Me, NBoc) | 4a | 48 | 80 | 93 |
| (indole with NHBoc tether, N-Allyl) | 3b | (fluorinated pyrroloindoline, N-Allyl, NBoc) | 4b | 48 | 40 | 55 |
| (indole with NHBoc tether, N-Propargyl) | 3c | (fluorinated pyrroloindoline, N-Propargyl, NBoc) | 4c | 72 | 31 | 54 |
| (5-Me indole with NHBoc tether, N-Me) | 3d | (5-Me fluorinated pyrroloindoline, N-Me, NBoc) | 4d | 48 | 80 | 95 |
| (6-Me indole with NHBoc tether, N-Me) | 3e | (6-Me fluorinated pyrroloindoline, N-Me, NBoc) | 4e | 48 | 76 | 81 |
| (7-Me indole with NHBoc tether, N-Me) | 3f | (7-Me fluorinated pyrroloindoline, N-Me, NBoc) | 4f | 48 | 77 | 85 |
| (5-F indole with NHBoc tether, N-Me) | 3g | (5-F fluorinated pyrroloindoline, N-Me, NBoc) | 4g | 72 | 69 | 82 |
| (6-F indole with NHBoc tether, N-Me) | 3h | (6-F fluorinated pyrroloindoline, N-Me, NBoc) | 4h | 48 | 61 | 80 |

TABLE 7-continued

Results of Asymmetric Fluorocyclization for Substrate 3

| Substrate 3 | Product 4 | Reaction time (h) | Yield (%) | ee value (%) |
|---|---|---|---|---|
| 3i | 4i | 48 | 39 | 81 |
| 3j | 4j | 48 | 64 | 90 |
| 3k | 4k | 48 | 59 | 90 |
| 3l | 4l | 72 | 60 | 86 |
| 3m | 4m | 72 | 63 | 86 |
| 3n | 4n | 48 | 65 | 80 |
| 3o | 4o | 72 | 69 | 86 |
| 3p | 4p | 72 | 75 | 77 |

TABLE 7-continued

Results of Asymmetric Fluorocyclization for Substrate 3

| Substrate 3 | | Product 4 | | Reaction time (h) | Yield (%) | ee value (%) |
|---|---|---|---|---|---|---|
| (MeO-substituted tryptamine NHTs) | 3q | (fluorocyclized product NTs) | 4q | 72 | 67 | 89 |
| (Mes-substituted tryptamine NHTs) | 3r | (fluorocyclized product NTs) | 4r | 72 | 63 | 93 |
| (Me-substituted tryptamine NHTs) | 3s | (fluorocyclized product NTs) | 4s | 72 | 68 | 84 |
| (tryptophol, N-Me) | 3aa | (fluorocyclized furoindoline, N-Me) | 4aa | 48 | 72 | 91 |
| (tryptophol, N-Et) | 3ab | (fluorocyclized furoindoline, N-Et) | 4ab | 48 | 68 | 86 |
| (tryptophol, N-Allyl) | 3ac | (fluorocyclized furoindoline, N-Allyl) | 4ac | 48 | 64 | 77 |
| (5-Ph tryptophol, N-Me) | 3ad | (fluorocyclized furoindoline, 5-Ph, N-Me) | 4ad | 72 | 67 | 92 |
| (6-Ph tryptophol, N-Me) | 3ae | (fluorocyclized furoindoline, 6-Ph, N-Me) | 4ae | 72 | 70 | 86 |

TABLE 7-continued

Results of Asymmetric Fluorocyclization for Substrate 3

| Substrate 3 | | Product 4 | | Reaction time (h) | Yield (%) | ee value (%) |
|---|---|---|---|---|---|---|
| | 3af | | 4af | 48 | 62 | 88 |
| | 3ag | | 4ag | 72 | 63 | 85 |
| | 3ah | | 4ah | 72 | 60 | 64 |
| | 3ai | | 4ai | 48 | 61 | 94 |
| | 3aj | | 4aj | 48 | 70 | 96 |
| | 3ak | | 4ak | 72 | 68 | 96 |
| | 3al | | 4al | 48 | 69 | 94 |
| | 3am | | 4am | 48 | 70 | 91 |

TABLE 7-continued

Results of Asymmetric Fluorocyclization for Substrate 3

| Substrate 3 | Product 4 | Reaction time (h) | Yield (%) | ee value (%) |
|---|---|---|---|---|
| 3an 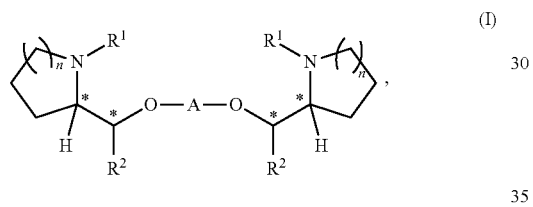 | 4an | 72 | 65 | 99 |

Although particular embodiments and examples have been herein described in detail, the above description has been done by way of example for purposes of illustration only, and is not intended to be limiting with respect to the scope of the invention. In particular, it is contemplated by the inventor that various substitutions, alterations, and modifications may be made to the invention without departing from the spirit and scope of the invention as claimed.

The invention claimed is:

1. A chiral bisamino-ether compound, having a structure of formula (I):

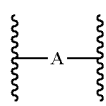
(I)

wherein:
n=1 or 2; chiral center * has (R) or (S) configuration; and

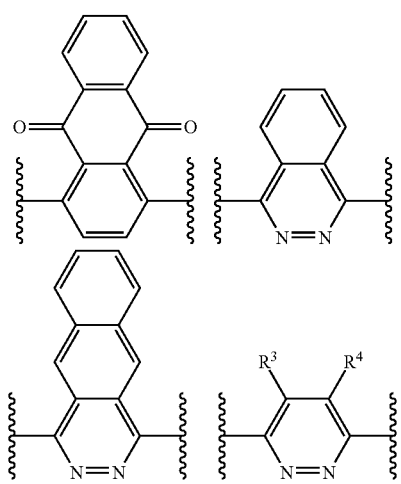

is one of the following moieties:

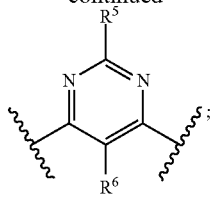

$R^1$ is selected from the group consisting of hydrogen, $C_1$-$C_8$ alkyl, unsaturated alkyl, and haloalkyl;

$R^2$ is selected from the group consisting of hydrogen, $C_1$-$C_8$ alkyl, phenyl, $C_1$-$C_8$ alkyl substituted phenyl, halophenyl, $C_1$-$C_8$ alkoxyl substituted phenyl, and naphthyl;

$R^3$ and $R^4$ may be the same or different, and are each independently selected from the group consisting of hydrogen and $C_1$-$C_8$ alkyl;

$R^5$ and $R^6$ may be the same or different, and are each independently selected from the group consisting of hydrogen, $C_1$-$C_8$ alkyl, haloalkyl, halogen, phenyl, $C_1$-$C_8$ alkyl substituted phenyl, halophenyl, and naphthyl;

wherein, the $C_1$-$C_8$ alkyl is methyl, ethyl, n-propyl, isopropyl, cyclopropyl, n-butyl, isobutyl, sec-butyl, tert-butyl, cyclobutyl, n-pentyl, isoamyl, neopentyl, sec-pentyl, tert-amyl, cyclopentyl, n-hexyl, isohexyl, neohexyl, sec-hexyl, tert-hexyl, cyclohexyl, n-heptyl, isoheptyl, neoheptyl, n-heptyl, tert-heptyl, cycloheptyl, n-octyl, isooctyl, neooctyl, sec-octyl, tert-octyl, or cyclooctyl;

wherein, the $C_1$-$C_8$ alkoxy is methoxyl, ethoxyl, n-propoxyl, isopropoxyl, cyclopropoxyl, n-butoxyl, iso-butoxyl, tert-butoxyl, cyclobutoxyl, n-pentyloxyl, iso-pentyloxyl, neo-pentyloxyl, sec-pentyloxyl, tert-pentyloxyl, cyclopentyloxyl, n-hexyloxyl, iso-hexyloxyl, neo-hexyloxyl, sec-hexyloxyl, tert-hexyloxyl, cyclohexyloxyl, n-heptyloxyl, iso-heptyloxyl, neo-heptyloxyl, sec-heptyloxyl, tert-heptyloxyl, cycloheptyloxyl, n-octyloxyl, iso-octyloxyl, neo-octyloxyl, sec-octyloxyl, tert-octyloxyl, or cyclooctyloxyl.

2. The chiral bisamino-ether compound of claim 1, wherein:
the $C_2$-$C_9$ unsaturated alkyl is allyl, 2 methylpropenyl, trans-2-butenyl, 3,3-dimethylallyl, trans-2-pentenyl, or propargyl;
the haloalkyl is halogenated alkyl with halogen being fluorine, chlorine, bromine or iodine.

3. The chiral bisamino-ether compound of claim 1, wherein the compound is a racemate, dextroisomer or laevoisomer having same chemical formula but different stereo structures and optical rotation properties.

4. A chiral bisamino-ether compound, the compound being selected form the group consisting of:

1,4-Bis((R)-((S)-1-methyl-2-pyrrolyl)(1-naphthyl) methoxy)phthalazine (Ia);
1,4-Bis((R)-((S)-1-allyl-2-pyrrolyl)(1-naphthyl)methoxy) phthalazine (Ib);
1,4-Bis((R)-(2-methoxyphenyl)((S)-1-methyl-2-pyrrolyl) methoxy)phthalazine (Id);
4,6-Bis((R)-((S)-1-methyl-2-pyrrolyl)(1-naphthyl) methoxy)-2,5-diphenylpyrimidine (Ie);
4,6-Bis((R)-((S)-1-allyl-2-pyrrolyl)(1-naphthyl) methoxy)-2,5-diphenylpyrimidine (If);
1,4-Bis((R)-((S)-1-methyl-2-piperidinyl)(1-naphthyl) methoxy)phthalazine (Ig);
1,4-Bis((R)-((S)-1-allyl-2-piperidyl)(1-naphthyl) methoxy)phthalazine (Ih);
3,6-Bis((R)-((5)-1-methyl-2-piperidinyl)(1-naphthyl) methoxy)pyridazine (Ii);
4,6-Bis((R)-((S)-1-methyl-2-piperidyl)(1-naphthyl) methoxy)-2,5-diphenylpyrimidine (Ij);
2-Methyl-4,6-bis((R)-((S)-1-methyl-2-piperidinyl)(1-naphthyl)methoxy)pyrimidine (Ik);
1,4-Bis((R)-(1-naphthyl)((S)-1-propyl-2-piperidyl) methoxy)phthalazine (Il);
4,6-Bis((R)-((S)-1-allyl-2-piperidyl)(1-naphthyl) methoxy)-2-methylpyrimidine (Im);
3,6-Bis((R)-((S)-1-allyl-2-piperidyl)(1-naphthyl) methoxy)pyridazine (In);
1,4-Bis((S)-((S)-1-methyl-2-pyrrolyl)(phenyl)methoxy) phthalazine (Io);
1,4-Bis((S)-((S)-1-methyl-2-pyrrolyl)(1-naphthyl) methoxy)phthalazine (Ip);
1,4-Bis((S)-((5)-1-allyl-2-pyrrolyl)(1-naphthyl)methoxy) phthalazine (Iq);
4,6-bis((S)-((S)-1-methyl-2-pyrrolyl)(1-naphthyl) methoxy)-2,5-diphenylpyrimidine (Is);
4,6-bis((S)-((S)-1-allyl-2-pyrrolyl)(1-naphthyl) methoxy)-2,5-diphenylpyrimidine (It);
1,4-bis((S)-((S)-1-methyl-2-piperidinyl)(1-naphthyl) methoxy)phthalazine (Iu);
4,6-Bis((S)-((S)-1-methyl-2-piperidinyl)(1-naphthyl) methoxy)-2,5-diphenylpyrimidine (Iv);
1,4-Bis((S)-((S)-1-methyl-2-piperidyl)(1-naphthyl) methoxy)-9,10-nonanedione (Iw);
1,4-Bis((R)-((R)-1-allyl-2-piperidyl)(1-naphthyl) methoxy)phthalazine (Ix); and
1,4-Bis((S)-((R)-1-allyl-2-piperidyl)(1-naphthyl) methoxy)phthalazine (Iy).

\* \* \* \* \*